US00PP34524P2

(12) United States Plant Patent
Trees

(10) Patent No.: US PP34,524 P2
(45) Date of Patent: Aug. 30, 2022

(54) ***LANTANA* PLANT NAMED 'SAILAN002'**

(50) Latin Name: *Lantana camara*
Varietal Denomination: SAILAN002

(71) Applicant: Sakata Seed America, Inc., Morgan Hill, CA (US)

(72) Inventor: Scott C. Trees, Arroyo Grande, CA (US)

(73) Assignee: Sakata Seed America, Inc., Morgan Hill, CA (US)

( * ) Notice: Subject to any disclaimer, the term of this patent is extended or adjusted under 35 U.S.C. 154(b) by 0 days.

(21) Appl. No.: 17/496,060

(22) Filed: Oct. 7, 2021

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./227
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new *Lantana* plant designated 'SAILAN002' particularly distinguished by semi-mounding growth habit, white flower color with yellow near the throat that fades away with age; and excellent heat tolerance is disclosed.

2 Drawing Sheets

Genus and species: *Lantana camara.*
Variety denomination: 'SAILAN002'.

BACKGROUND

The present invention relates to a new and distinct cultivar of *Lantana* plant botanically known as *Lantana camara* and hereinafter referred to by the cultivar name 'SAILAN002'.

The new cultivar originated in a controlled breeding program in Guadalupe, Calif. during June 2017. The objective of the breeding program was the development of *Lantana* cultivars with a semi-mounded growth habit, white flower color and excellent heat tolerance.

The new *Lantana* cultivar is the result of cross-pollination. The female (seed) parent of the new cultivar is the proprietary *Lantana camara* breeding selection coded '3566-B-2', not patented, characterized by its light orange colored inflorescences, medium green colored foliage, and vigorous, semi-upright growth habit. The male (pollen) parent of the new cultivar is the proprietary *Lantana camara* breeding selection coded '18265', not patented, characterized by its medium pink colored inflorescences, medium green colored foliage, and moderately vigorous, compact growth habit. The new cultivar was selected as a single flowering plant within the progeny of the above stated cross-pollination during May 2018 in a controlled environment in Guadalupe, Calif.

Asexual reproduction of the new cultivar by terminal stem cuttings since May 2018 in Guadalupe, Calif. and Arroyo Grande, Calif. has demonstrated that the new cultivar reproduces true to type with all of the characteristics, as herein described, firmly fixed and retained through successive generations of such asexual propagation.

SUMMARY

The following characteristics of the new cultivar have been repeatedly observed and can be used to distinguish 'SAILAN002' as a new and distinct cultivar of *Lantana* plant:

1. Semi-mounding growth habit;
2. White flower color with yellow near the throat that fades away with age; and
3. Excellent heat tolerance.

BRIEF DESCRIPTION OF THE PHOTOGRAPHS

The accompanying photographs, taken on Sep. 16, 2020 in Salinas, Calif. which show, as nearly true as it is reasonably possible to make the same in color illustrations of this type, typical flower and foliage characteristics of the new cultivar. Colors in the photographs may differ slightly from the color values cited in the detailed description, which accurately describes the colors of 'SAILAN002'.

DETAILED BOTANICAL DESCRIPTION

Figure 1:
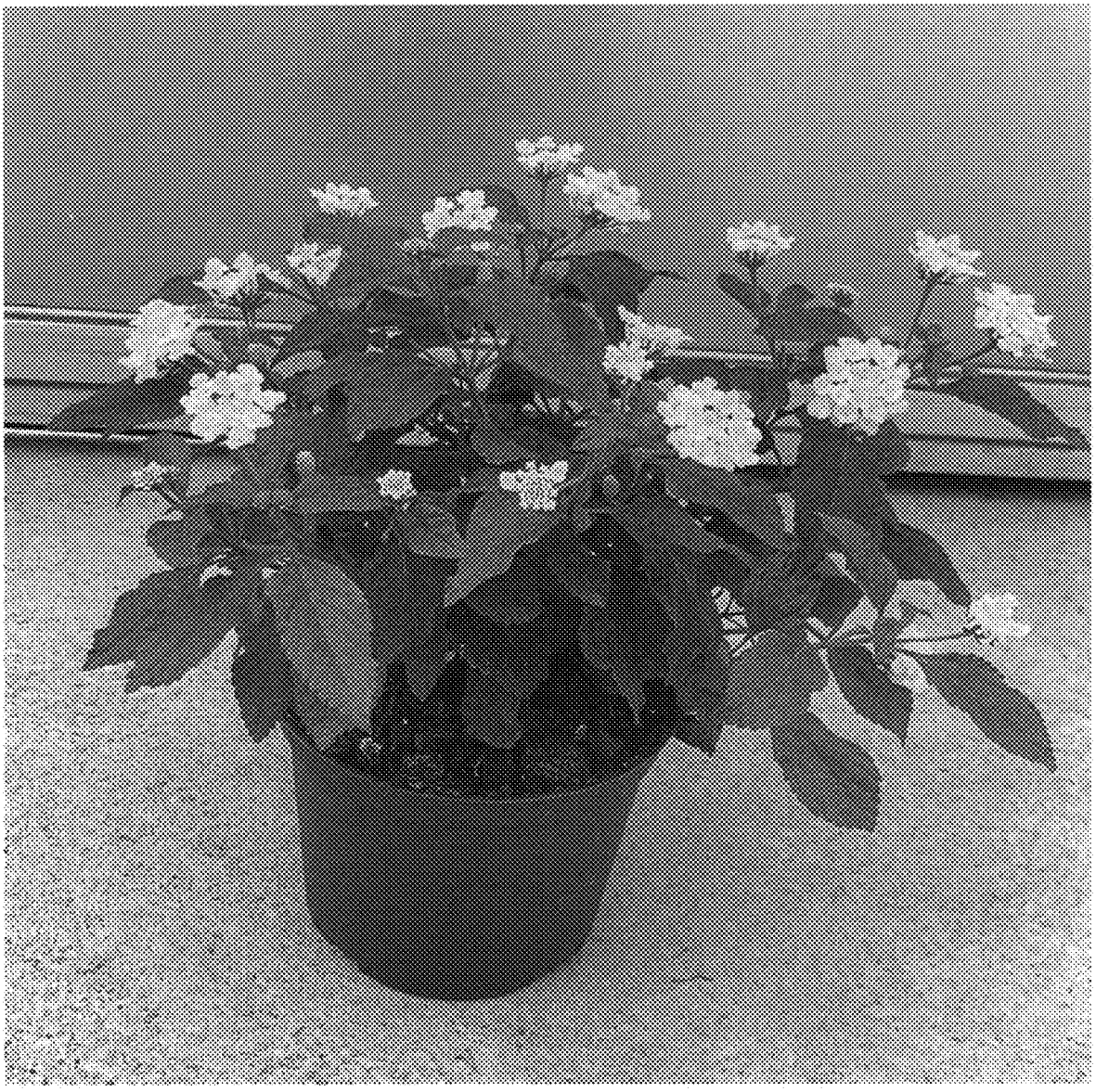
FIG. 1 illustrates a side view of the overall growth and flowering habit of 'SAILAN002'.
Figure 2:
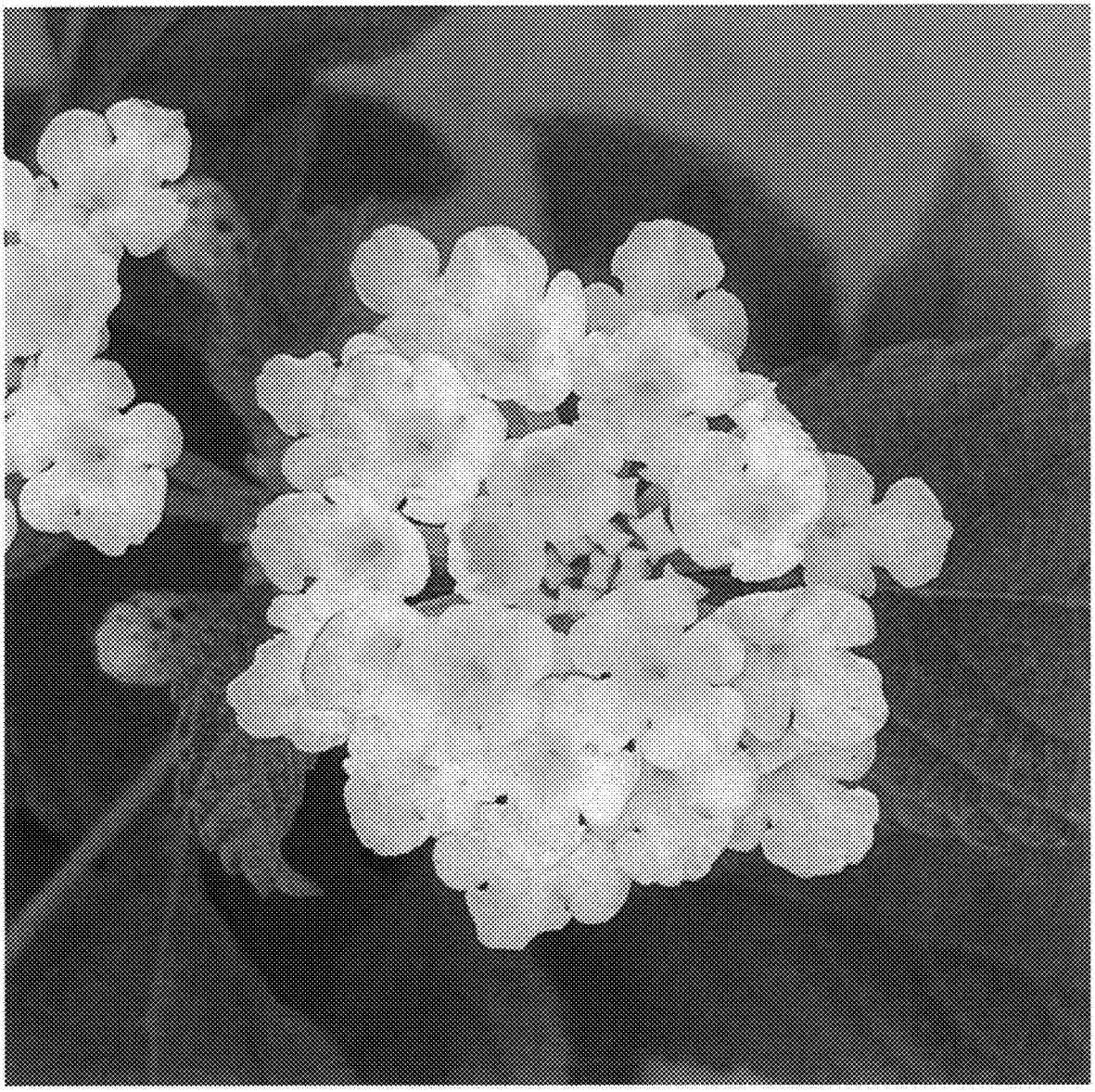
FIG. 2 illustrates a close-up view of an individual inflorescence of 'AILAN002'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used.

The following descriptions and measurements were collected in September of 2020 and obtained from plants grown 4.25 months from transplant into 6-inch pots from rooted cuttings in Salinas, Calif., under greenhouse conditions.

Botanical classification:

*Genus and species.*—*Lantana camara.*
*Variety.*—'SAILAN002'.
*Parentage.*—Female parent: '3566-B-2', not patented. Male parent: '18265', not patented.

Growth:

*Type cutting*.—Terminal stem.

*Time to initiate roots*.—Approximately 7 to 11 days.

*Time to produce a rooted cutting*.—Approximately 35 to 42 days.

*Root description*.—Fibrous; woody.

*Rooting habit*.—Freely branching. The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24C.

Plant description:

*Commercial crop time*.—Approximately 6 to 7 weeks from a rooted cutting to finish in a 10 cm pot.

*Growth habit and general appearance*.—Moderately vigorous, semi-upright.

*Height from soil level to top of plant plane*.—Approximately 16.0 cm.

*Width*.—Approximately 35.0 cm.

*Branching habit*.—Freely branching, pinching enhances branching.

*Quantity of lateral branches per plant*.—2.

Branch:

*Shape*.—Square in cross section.

*Strength*.—Strong, becomes woody with age.

*Length*.—Approximately 12.0 cm to 14.0 cm.

*Diameter*.—Approximately 6.0 mm.

*Length of central internode*.—Approximately 2.0 cm.

*Texture*.—Densely pubescent, short rough pubescence.

*Gland color*.—Colorless, transparent.

*Color of young stem*.—144A (Strong Yellow Green).

*Color of mature stem*.—Closest to 177B (Light Reddish Brown).

Foliage description:

*Quantity of leaves per lateral branch*.—Approximately 15.

*Fragrance*.—None.

*Form*.—Simple.

*Arrangement*.—Opposite.

*Aspect*.—Perpendicular to or acute angle to stem.

*Shape*.—Ovate.

*Margin*.—Serrate.

*Apex*.—Acuminate.

*Base*.—Obtuse.

*Venation pattern*.—Entire.

*Length of mature leaf*.—Approximately 6.5 cm.

*Width of mature leaf*.—Approximately 3.2 cm.

*Texture of upper surface*.—Scabrous.

*Texture of lower surface*.—Scabrous and glandular pubescent along venation.

*Gland color*.—Not Observed.

*Vein color upper*.—145A (Strong Yellow Green).

*Vein color lower*.—145B (Light Yellow Green).

*Color of upper surface*.—Closest to but darker than NN137A (Greyish Olive Green).

*Color of lower surface*.—Closest to but darker than 147B (Moderate Yellow Green).

Petiole:

*Length*.—Approximately 16.0 mm.

*Diameter*.—Approximately 2.0 mm.

*Texture*.—Scabrous and glandular pubescent.

*Gland color*.—Not Observed.

*Color*.—143A (Strong Yellow Green).

Flowering description:

*Flowering habit*.—'SAILAN002' is freely flowering under outdoor growing conditions with substantially continuous blooming from spring through autumn and year-round in greenhouse environment.

*Lastingness of individual inflorescence on the plant*.—Approximately 7 to 10 days from first color of outer buds to dropping of last flower.

Inflorescence description:

*Type*.—Umbel.

*Quantity per plant*.—Approximately 20 to 25.

*Fragrance*.—Strong, spicy.

*Aspect*.—Facing upward or outward.

*Height*.—Approximately 1.5 cm.

*Width*.—Approximately 3.5 cm.

*Quantity of fully open flowers per inflorescence*.—Up to 26.

Peduncle:

*Strength*.—Strong; flexible.

*Shape*.—Square in cross section.

*Aspect*.—Acute angle to stem.

*Length*.—Approximately 2.5 cm to 4.0 on mature influences.

*Diameter*.—Approximately 1.0 mm to 2.0 mm.

*Texture*.—Scabrous and glandular pubescent.

*Gland color*.—Transparent.

*Color*.—144A (Strong Yellow Green).

Flower description:

*Type*.—Salverform.

Bud:

*Rate of opening*.—Generally takes 1 to 2 days for bud to progress from first color to fully open flower. Buds open in progression from the margin to the center of the inflorescence.

*Quantity of unopened inflorescences per plant*.—Approximately 10.

*Shape*.—Elongated, rectangular at apex.

*Length*.—Approximately 7.0 mm.

*Diameter*.—Approximately 3.0 mm.

*Color*.—2D (Pale Greenish Yellow).

Corolla:

*Depth*.—Approximately 1.0 mm.

*Diameter*.—Approximately 9.0 mm.

Petals:

*Quantity*.—4

*Description*.—Non-imbricate, non-symmetrical petals. Petals are fused at base forming a corolla tube.

*Shape*.—Obovate.

*Appearance*.—Dull.

*Aspect*.—Cupped.

*Margin*.—Entire, ruffled.
*Apex*.—Obtuse; rounded.
*Length of upper petal from throat*.—Approximately 4.0 mm.
*Width of upper petal*.—Approximately 6.0 mm.
*Length of lateral petals from throat*.—Approximately 3.5 mm.
*Width of lateral petals*.—Approximately 4.0 mm.
*Length of lower petal from throat*.—Approximately 4.0 mm.
*Width of lower petal*.—Approximately 6.5 mm.
*Texture of upper and lower surface*.—Glabrous.
*Gland color*.—Not Observed.
*Color of upper surface*.—NN155D (White) with 7A (Brilliant Yellow) near throat that fades away as flowers age.
*Color of lower surface*.—NN155D (White).

Corolla tube:
*Length*.—Approximately 1.0 cm.
*Diameter at midpoint*.—Approximately 1.5 mm.
*Texture of inner and outer surface*.—Glabrous.
*Pubescence color*.—None.
*Color of inner surface*.—155C (White).
*Color of outer surface*.—155A (White).

Calyx:
*Shape*.—Tubular with two broadly acute tips.
*Length*.—Approximately 2.5 mm.
*Diameter*.—Approximately 1.5 mm.
*Texture of inner surface*.—Glabrous.
*Texture of outer surface*.—Transparent.
*Gland color*.—Transparent.
*Color of inner and outer surfaces*.—145C (Light Yellow Green).

Bracts:
*Quantity per flower*.—1 per flower.
*Shape*.—Linguate.
*Length*.—Approximately 6.0 mm.
*Width*.—Approximately 1.5 mm.
*Texture of upper and lowers surface*.—Slightly pubescent.
*Color of upper and lower surfaces*.—Closest to but darker than 143A (Strong Yellow Green) at apex lightening to 143C (Strong Yellow Green) at base.

Reproductive organs:
*Androecium*.—Stamen quantity: 4 per flower, adnate to corolla tube. Stamen length: Approximately 1.0 mm. Anther shape: Bilobed, ovoid. Anther length: Approximately less than 1.0 mm. Anther color: 163B (Strong Orange Yellow). Pollen amount: Very sparse. Pollen Color: 20A (Brilliant Yellow).
*Gynoecium*.—Pistil quantity: 1 per flower. Pistil length: Approximately 3.0 mm. Stigma shape: Funnel. Stigma length: Less than 1.0 mm. Stigma color: 144A (Strong Yellow Green). Style length: Approximately 2.5 mm. Style color: 155C (Greenish White). Ovary diameter: Approximately 1.0 mm. Ovary color: N144C (Strong Yellow Green).

Seed and fruit production: Neither seed nor fruit production has been observed.

Disease and pest resistance: Resistance to pathogens and pests common to *Lantana* has not been observed.

COMPARISON OF 'SAILAN002' WITH PARENTAL LINES AND KNOWN VARIETY

'SAILAN002' is distinguished from the parental lines as described in Table 1.

TABLE 1

Comparison with Parental Lines

| Trait | Variety 'SAILAN002' | Female parent '3566-B-2' | Male parent '18265' |
|---|---|---|---|
| Inflorescense color | White | Light orange | Medium pink |
| Growth habit | Semi-mounding | Semi-upright | Compact |

'SAILAN002' can be compared to the commercial *Lantana* variety 'Ban Whit' (U.S. Plant Pat. No. 21,590). Differences between the varieties are described in Table 2.

TABLE 2

Comparison with Similar Variety

| | 'SAILAN002' | 'Ban Whit' |
|---|---|---|
| Leaf color upper | Darker than NN137A (Greyish Olive Green) | Darker than 147A (Moderate Olive Green) |
| Bud Color | 2D (Pale Greenish Yellow) | 12C (Light Yellow) |
| Color of Upper Surface | NN155D (White) with 7A (Brilliant Yellow) near throat that fades away as flowers age. | RHS 155D but much whiter, with RHS 14B at the corolla opening, as well as a narrow band of RHS 9A; finally, all flowers then show very little yellow color at the corolla opening. |

I claim:

1. A new and distinct cultivar of *Lantana* Plant Named 'SAILAN002' as described and illustrated herein.

* * * * *